United States Patent
Rijpers et al.

(10) Patent No.: US 9,116,086 B2
(45) Date of Patent: Aug. 25, 2015

(54) DEPOSITION METHOD AND APPARATUS

(75) Inventors: Bartolomeus Petrus Rijpers, Nuenen (NL); Jurriaan Hendrik Koenraad Van Schaik, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 656 days.

(21) Appl. No.: 12/816,733

(22) Filed: Jun. 16, 2010

(65) Prior Publication Data

US 2010/0330280 A1   Dec. 30, 2010

Related U.S. Application Data

(60) Provisional application No. 61/221,279, filed on Jun. 29, 2009.

(51) Int. Cl.
  *G01N 1/28*   (2006.01)

(52) U.S. Cl.
  CPC .................................. *G01N 1/2813* (2013.01)

(58) Field of Classification Search
  USPC .................. 427/259, 261, 265; 977/881, 892; 250/311
  See application file for complete search history.

(56) References Cited

U.S. PATENT DOCUMENTS

| 4,015,986 | A | * | 4/1977 | Paal et al. ..................... 430/323 |
| 4,420,365 | A | * | 12/1983 | Lehrer .......................... 438/702 |
| 5,127,574 | A | * | 7/1992 | Mosser et al. ............... 236/44 R |
| 7,282,238 | B2 | * | 10/2007 | Shanmugham et al. ...... 427/223 |
| 7,317,188 | B2 | * | 1/2008 | Zhang et al. .................. 250/307 |
| 7,335,395 | B2 | * | 2/2008 | Ward et al. ................... 427/198 |
| 7,758,794 | B2 | * | 7/2010 | Chou et al. ................... 264/319 |
| 7,955,486 | B2 | * | 6/2011 | Yu et al. ........................ 205/133 |
| 2002/0134938 | A1 | * | 9/2002 | Chang et al. ................. 250/311 |
| 2007/0093044 | A1 | * | 4/2007 | Rijpers et al. ................ 438/584 |
| 2008/0095921 | A1 | * | 4/2008 | O'Connor et al. .......... 427/2.28 |

OTHER PUBLICATIONS

Rijpers, B., et al., "Automated TEM Sample Preparation on Wafer Level for Metrology and Process Control," Proceedings of the 33rd International Symposium for Testing and Failure Analysis, Nov. 2007; pp. 107-114.

* cited by examiner

*Primary Examiner* — Alex A Rolland
(74) *Attorney, Agent, or Firm* — Sterne, Kessler, Goldstein & Fox P.L.L.C (57) ABSTRACT

A method for depositing a protective layer of material on a localized area on a substrate, such as a pattern of photo resist, includes forming a controlled environment around the substrate and positioning a hollow needle adjacent to the localized area on the substrate. A liquid comprising the material is directed through the hollow needle onto the localized area, so as to deposit a layer of the material on the localized area. The layer of material may act as a Z-contrast forming layer in TEM.

11 Claims, 4 Drawing Sheets

DEPOSITION METHOD AND APPARATUS

CROSS REFERENCE TO RELATED APPLICATIONS

This application claims the benefit under 35 U.S.C. 119(e) to U.S. Provisional Patent Application No. 61/221,279, file Jun. 29, 2009, which is incorporated by reference herein in its entirety.

BACKGROUND

1. Field of the Invention

The present invention relates to methods and apparatus for depositing a layer on a localized area on a substrate. The invention has particular, although not exclusive application for use in a metrology method for use in a lithographic method for manufacturing a device.

2. Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (photo resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In order to monitor the lithography process it is necessary to measure the dimensions of topographical features present on a substrate, which has been processed in the lithographic apparatus, for example the width of lines of a pattern formed on the photo resist by the lithography process. This may be performed using a Transmission Electronic Microscope (TEM), in which case it is necessary to deposit an electrically conductive layer over the photo resist.

SUMMARY

Therefore, what is needed is a method of providing a layer formed over a photoresist pattern, the layer being registerable by a TEM and avoiding damage to the photoresist pattern.

According to an embodiment of the invention, there is provided a method for depositing a protective layer of material on a localized area on a substrate comprising the following steps. Forming a controlled environment around the substrate. Positioning a liquid directing device carrying a liquid comprising the material adjacent the localized area on the substrate. Directing the liquid comprising the material through the liquid directing device onto the localized area, so as to deposit a layer of the material on the localized area.

According to a further embodiment of the invention, there is provided a deposition apparatus for preparing a protective layer on a localized area on a substrate comprising an arrangement, a liquid directing device, a positioning arrangement, and a liquid injection arrangement. The arrangement is effective to define a controlled environment around the substrate. The positioning arrangement is effective to position the hollow needle adjacent the localized area on the substrate. The liquid injection arrangement is effective to enable a liquid comprising a material to be deposited to pass through the hollow needle onto the localized area, so as to deposit a layer of the material on the localized area.

According to a yet further embodiment of the present invention, there is provided a method of forming a lamella for use in a transmission electron microscope comprising the following steps. Depositing a protective layer of material on a localized area on a substrate by: forming a controlled environment around the substrate, positioning a liquid directing device carrying a liquid comprising the material adjacent the localized area on the substrate, and directing the liquid comprising the material through the liquid directing device onto the localized area, so as to deposit a layer of the material on the localized area.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the present invention and, together with the description, further serve to explain the principles of the invention and to enable a person skilled in the relevant art(s) to make and use the invention.

The features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Before describing such embodiments in more detail, however, it is instructive to present an example environment in which embodiments of the present invention may be implemented.

Figure 1:
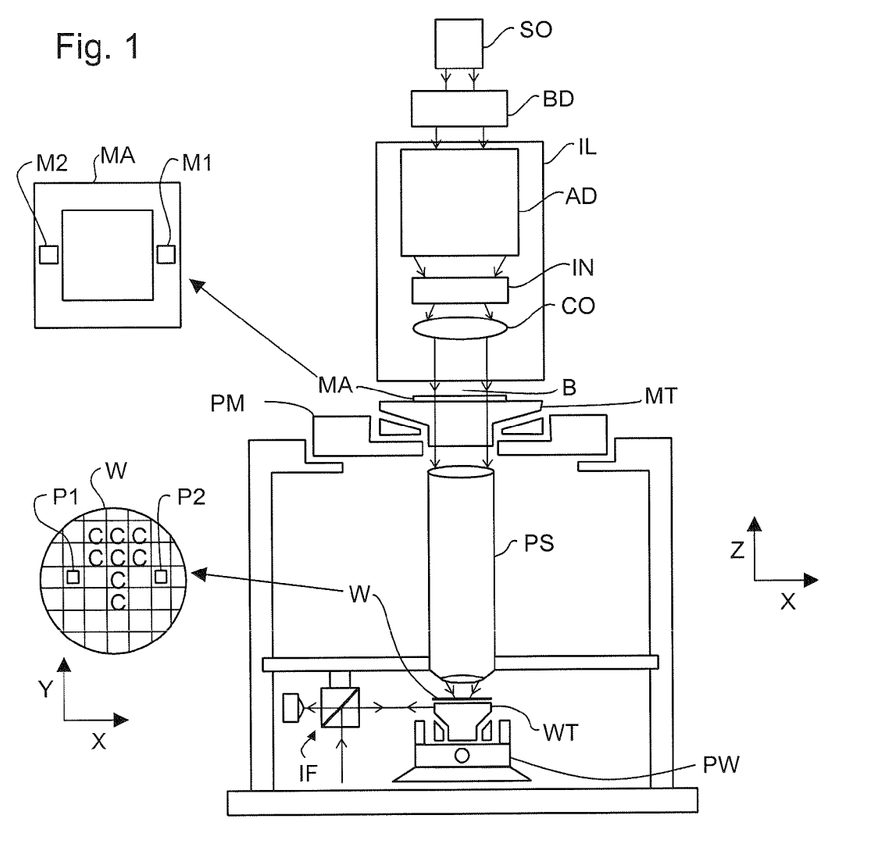
FIG. 1 depicts a lithographic apparatus which may be used in a method, according to an embodiment of the invention.

FIG. 1 schematically depicts a lithographic apparatus according to one embodiment of the invention. The apparatus comprises an illumination system (illuminator) IL configured to condition a radiation beam B (e.g., UV radiation); a support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

An exemplary system and method is discussed in a co-owned, co-pending application, U.S. Published Patent Application No. 2007/0093044 ("the '044 publication"), the contents of which are hereby incorporated by reference, there is disclosed a method of depositing a metal layer on a layer of photo resist deposited on a substrate, in which a gas is activated using a particle beam, such as an electron beam.

Figure 2:
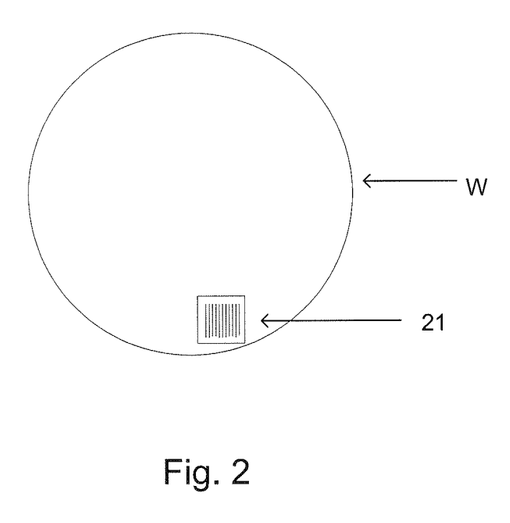
FIG. 2 illustrates schematically an embodiment of a test target comprising a series of lines formed in photo resist on a substrate produced by the apparatus of FIG. 1.

Referring now to FIG. 2 this figure illustrates schematically a pattern of lines formed in photo resist produced by a lithographic apparatus, such as that disclosed above. It will be appreciated that the relative scales of the pattern and the wafer have been changed for the sake of clarity, as typically the pattern will have an area of about 400×400 nm. In one example, conductive metal layer is placed over the photoresist so that the pattern can be monitored using a TEM. As explained below, the smallest possible pitch which can be effectively monitored using the prior art method of using a conductive metal layer is about 80 nm (having, for example, a line thickness of about 40 nm).

Figure 3:
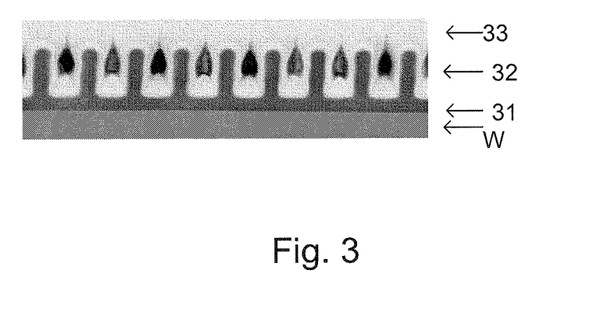
FIG. 3 illustrates a STEM image of a wafer carrying a series of lines of photo resist deposited on a substrate, the lines having about a 50 nm critical dimension (CD), according to an embodiment of the invention.
Figure 4:
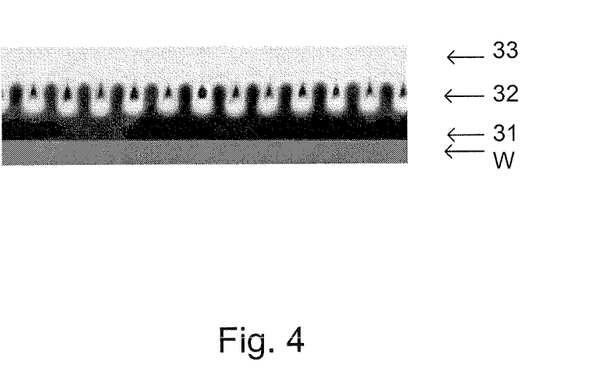
FIG. 4 illustrates a STEM image of a wafer carrying an equivalent structure to that shown in FIG. 3, the lines having a CD of about 40 nm, according to an embodiment of the invention.
Figure 5:
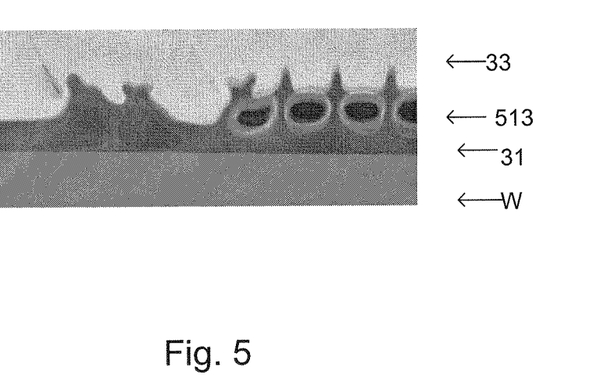
FIG. 5 illustrates a STEM image of a wafer carrying two layers of photo resist formed on a substrate, the patterns in each layer being offset and having a CD of about 32 nm, according to an embodiment of the invention.

FIGS. 3, 4 and 5 show STEM images of the structures in which a layer of Platinum is deposited over the pattern. For example, structures using an e-beam deposition process disclosed in the '044 publication. In these figures, equivalent structures are indicated by the same reference numerals, for the sake of clarity.

FIG. 3 illustrates a cross section STEM image of a wafer W of one embodiment, on which a bottom antireflective coating (BARC) layer 31 of photo resist has been deposited. This carries a layer of photo resist which has been patterned in the lithography apparatus, using the mask MA, to produce a series of substantially 50 nm width parallel lines 32 at a pitch of about 100 nm. Over the pattern of lines 32, there is formed a localized layer 33 of Platinum using the e-beam deposition process, for example as disclosed in the '044 publication. In the particular pattern disclosed in FIG. 3, the STEM image indicates that the overall profile is acceptable, no damage to the underlying BARC layer 31 being observable.

The cross section STEM image illustrated in FIG. 3, however, can be compared with the corresponding image shown in FIG. 4 in which the pitch of the about 40 nm width photo resist lines is about 80 nm. In this case the underlying BARC layer 31 has curved due to the effect of the e-beam. Furthermore, it has be found that the measured film thickness (FT) of the photoresist layer deviates from the value measured using scatterometry by, for example, about 14%. This variation in thickness will lead to unacceptable measurement errors in the measured parameters.

Turning now to FIG. 5, this figure illustrates a pattern in the photoresist with about 32 nm width lines 51, 52, each having a pitch of about 64 nm. As can be seen from this STEM image, deposition of the Platinum layer 33 using an e-beam, has caused the photo resist layer 51 to melt, causing total collapse of the photo resist structure.

In accordance with an embodiment of the invention, before using e-beam deposition to produce an electrically conductive layer over the photo resist pattern, a localized area of a protective material is formed over the layer, or layers, of photo resist pattern, using microinjection under a humidity controlled environment. In one example, the layer of material is a Z-contrast forming layer, such as material comprising a high atomic number substance. Such a layer will avoid damage to the photo resist, even for narrow line widths. Also, this layer may result in contrast difference between the photo resist and the protective layer, which results in Z-contrast in a TEM. Good contrast difference is important for accurate metrology in a TEM.

Figure 6:
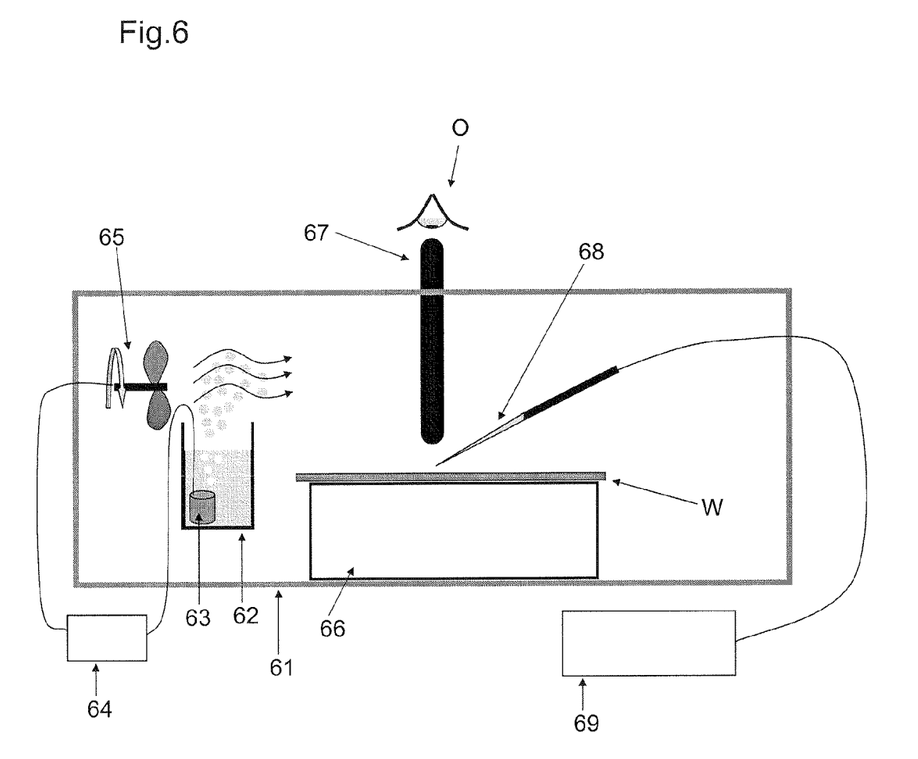
FIG. 6 illustrates an embodiment of a microinjection apparatus for use in a process in accordance with an embodiment of the invention.

Referring now to FIG. 6, this figure illustrates a microinjection apparatus in accordance with an embodiment of the invention. The apparatus is positioned in a half sealed chamber 61 in which is positioned a container 62 of a suitable liquid, water being used in this particular example. A heater element 63, or other mist/fog making device, is positioned in the container 62, an electrical source 64 being provided outside the chamber 61, the electrical source being effective to control the electrical supply to the heater such that the water in the container vaporizes to provide a suitable moist environment within the enclosure 61. A fan 65 is provided to distribute the water mist within the chamber 61.

Within the chamber 61 there is provided a sample holder 66, on which a wafer W carrying a photo resist pattern on which it is required to deposit a protective layer may be placed. An optical microscope 67 is positioned so as to enable an observer O outside the chamber 61 to view the pattern on the wafer W. A glass hollow needle, in the form of a micropipette 68 is provided within the chamber 61, the position of the micropipette being adjustable by a controller 69 under the control of the observer O.

In use of the microinjection apparatus, in accordance with an embodiment of a method of the invention, the glass micropipette 68 is used to deposit a metallic layer on the pattern on the wafer by means of a coating material carried within the glass pipette 68. The coating material may be Ferritin, an iron protein complex, resulting in an electrically conductive coating of Iron being deposited over the pattern on the wafer (as ferritin is not electrically conductive—it is an iron complex soluble in water). Another example of a suitable material is $KMnO_4$, in which case a coating of $KMnO_4$ crystals will be deposited over the pattern on the wafer.

In one example, using a method in accordance with the invention it is possible to deposit protective layers exhibiting Z-contrast over a controlled area (typically about 400×400 nm or larger), that is over patterns of photo resist lines having line widths of down to about 30 nm, without any damage to the underlying photo resist being caused. It will be appreciated that the use of the humidity-controlled environment within the chamber 61 prevents the surface of the wafer W from drying out during the deposition procedure. It will also be appreciated that the protective layer must be localized in the area of the line pattern on the photoresist, to enable automated pattern recognition in an automated FIB-SEM system for producing the TEM lamella in which the localized electrically conductive layer is formed over the line pattern.

It will be appreciated that many other materials may be used for the protective layer, for example water soluble metal complexes or metal containing materials. While such materials are not conductive, they will result in Z-formation contrast in use of the TEM. Doped non-conductive materials, such as paint doped with high atomic number materials, will also work. Indeed any water soluble material may be used as long as it does not dissolve the photoresist, although it should produce Z-contrast in TEM.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

While specific embodiments of the invention have been described above, it will be appreciated that the invention may be practiced otherwise than as described. For example, the invention may take the form of a computer program containing one or more sequences of machine-readable instructions describing a method as disclosed above, or a data storage medium (e.g., semiconductor memory, magnetic or optical disk) having such a computer program stored therein.

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for depositing a protective layer of material on a localized area on a substrate, the method comprising:
    forming a humidity controlled environment around the substrate to prevent a surface of the substrate from drying out during the deposition;
    positioning a micropipette carrying a liquid comprising the material adjacent the localized area on the substrate;
    directing the liquid through the micropipette onto the localized area, so as to deposit the protective layer of the material on the localized area, wherein in the localized area is a pattern of photoresist formed on the substrate; and
    forming an electrically conductive layer over the protective layer on the localized area using an e-beam deposition, wherein the substrate is configured to be inspected by a transmission electron microscope (TEM),
    whereby the electrically conductive layer protects the patterned photoresist during the TEM inspection and the protective layer of the material on the localized area protects the patterned photoresist during formation of the electrically conductive layer.

2. The method of claim 1, wherein the humidity controlled environment comprises water vapor.

3. The method of claim 1, wherein the material is Ferritin protein complex.

4. The method according to claim 1, wherein the liquid is a $KMnO_4$ solution in water.

5. The method of claim 1, wherein the pattern comprises a plurality of lines, each of the plurality of lines has a width of about 32 nm.

6. The method of claim 5, wherein each of the plurality of lines has a pitch of about 64 nm.

7. The method of claim 1, wherein the pattern comprises a plurality of lines, each of the plurality of lines has a width of about 40 nm.

8. The method of claim 7, wherein each of the plurality of lines has a pitch of about 80 nm.

9. The method of claim 1, wherein a contrast difference between the photo resist and the protective layer results in a Z-contrast in a transmission electron microscope (TEM).

10. A device manufacturing method comprising:
    transferring a pattern from a patterning device onto a localized area on a substrate;
    forming a humidity controlled environment around the substrate to prevent a surface of the substrate from drying out;
    positioning a micropipette carrying a liquid comprising a material adjacent the localized area on the substrate;
    directing the liquid through the micropipette onto the localized area, so as to deposit a protective layer of the material on the localized area, wherein in the localized area is a pattern of photo resist formed on the substrate; and
    forming an electrically conductive layer over the protective layer on the localized area using an e-beam deposition, wherein the substrate is configured to be inspected by a transmission electron microscope (TEM),
    whereby the electrically conductive layer protects the patterned photoresist during the TEM inspection and the protective layer of the material on the localized area protects the patterned photoresist during formation of the electrically conductive layer.

11. A method of forming a lamella for use in a transmission electron microscope, comprising:
    depositing a protective layer of material on a localized area on a substrate, by:
        forming a humidity controlled environment around the substrate to prevent a surface of the substrate from drying out during the depositing;
        positioning a micropipette carrying a liquid comprising the material adjacent the localized area on the substrate; and
        directing the liquid through the micropipette onto the localized area, so as to deposit the protective layer of the material on the localized area, wherein in the localized area is a pattern of photo resist formed on the substrate; and
    forming an electrically conductive layer over the protective layer on the localized area using an e-beam deposition, wherein the substrate is configured to be inspected by the transmission electron microscope (TEM),
    whereby the electrically conductive layer protects the patterned photoresist during the TEM inspection and the protective layer of the material on the localized area protects the patterned photoresist during formation of the electrically conductive layer.

* * * * *

UNITED STATES PATENT AND TRADEMARK OFFICE
CERTIFICATE OF CORRECTION

PATENT NO.        : 9,116,086 B2  
APPLICATION NO.   : 12/816733  
DATED             : August 25, 2015  
INVENTOR(S)       : Rijpers et al.

Page 1 of 1

It is certified that error appears in the above-identified patent and that said Letters Patent is hereby corrected as shown below:

In the claims

In column 10, line 1, claim 4, after "wherein the", please insert --non-charged--.

Signed and Sealed this  
Sixteenth Day of August, 2016

Michelle K. Lee  
*Director of the United States Patent and Trademark Office*